(12) United States Patent
Miller

(10) Patent No.: US 9,204,713 B2
(45) Date of Patent: Dec. 8, 2015

(54) PROCESS AND RESULTING PRODUCT FOR MATCHING A MOUTHPIECE FOR CLEANING TEETH TO A USER'S ORAL GEOMETRY

(75) Inventor: Kevin A. Miller, Bellevue, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 289 days.

(21) Appl. No.: 13/993,096

(22) PCT Filed: Dec. 16, 2011

(86) PCT No.: PCT/IB2011/055746
§ 371 (c)(1),
(2), (4) Date: Aug. 28, 2013

(87) PCT Pub. No.: WO2012/085799
PCT Pub. Date: Jun. 28, 2012

(65) Prior Publication Data
US 2013/0333133 A1  Dec. 19, 2013

Related U.S. Application Data

(60) Provisional application No. 61/424,731, filed on Dec. 20, 2010.

(51) Int. Cl.
*A61C 17/00* (2006.01)
*A46B 9/04* (2006.01)
*A61C 17/22* (2006.01)

(52) U.S. Cl.
CPC . *A46B 9/04* (2013.01); *A46B 9/045* (2013.01); *A61C 17/00* (2013.01); *A61C 17/22* (2013.01); *A61C 17/228* (2013.01); *A46B 2200/1066* (2013.01); *Y10T 29/49995* (2015.01)

(58) Field of Classification Search
CPC ........ A61C 19/063; A61C 7/08; A61C 17/22; A61C 17/222; A46B 9/045
USPC .................................................. 300/21; 433/6
See application file for complete search history.

(56) References Cited

U.S. PATENT DOCUMENTS

| | | |
|---|---|---|
| 4,399,582 A | 8/1983 | Ernest et al. |
| 5,683,243 A | 11/1997 | Andreiko et al. |
| 6,786,732 B2 | 9/2004 | Savill et al. |
| 7,771,195 B2 | 8/2010 | Knopp et al. |
| 2004/0128777 A1 | 7/2004 | Koh |
| 2005/0039280 A1* | 2/2005 | Trimmer et al. ............. 15/167.2 |
| 2005/0125918 A1 | 6/2005 | Brooks |
| 2008/0010771 A1 | 1/2008 | Hilscher et al. |

FOREIGN PATENT DOCUMENTS

| | | |
|---|---|---|
| DE | 2155909 A1 | 6/1972 |
| WO | 2007121760 A1 | 11/2007 |

* cited by examiner

*Primary Examiner* — Laura C Guidotti

(57) ABSTRACT

A method and the resulting product for optimizing the configuration of a mouthpiece for cleaning teeth in which the configuration of the mouthpiece is optimized to the oral geometry of individual users. The method includes a first step (26) of producing a digital scan of the oral geometry of the individual user and then producing a rigid shell (30) for the mouthpiece substantially matching the digital scan. The configuration of the resulting mouthpiece is characterized by the outer surface of the shell not extending from the buccal surface of the individual teeth more than 7 mm (31); further, by the rear edge of the shell not contacting the tissues to the rear of the rearmost teeth (36), and still further by no more than a 2 mm overlap into the gum line (36), when the mouthpiece is operatively positioned in the user's mouth.

8 Claims, 2 Drawing Sheets

PROCESS AND RESULTING PRODUCT FOR MATCHING A MOUTHPIECE FOR CLEANING TEETH TO A USER'S ORAL GEOMETRY

This invention relates generally to oral teeth cleaning appliances, in particular mouthpieces, and more particularly concerns providing such a mouthpiece configured to fit an individual user's particular oral geometry.

It is well known that each person has a unique, particular oral geometry, with its own special characteristics and dimensions. The wide variation in oral geometry presents some challenges for cleaning teeth with toothbrushes, both manual and power, but presents significant challenges for a mouthpiece appliance. In general, a mouthpiece can have advantages over toothbrushes in cleaning efficacy and speed of cleaning. However, the challenges presented by the differences in oral geometry affecting mouthpiece configurations have not heretofore been overcome by providing differing mechanical configurations or linkages which generally attempt to be able to adapt a generic mouthpiece to different oral geometries. Hence, mouthpiece appliances for oral cleaning have not been able to realize their full potential for improved efficacy and efficiency in cleaning while also maintaining comfort for the user.

Accordingly, disclosed herein is a method and resulting product for optimizing the configuration of a mouthpiece appliance for oral cleaning to the oral geometry of an individual user, comprising the steps of: scanning the oral geometry or portions thereof of an individual user; producing a rigid shell member for the mouthpiece substantially matching the oral geometry scan, wherein the resulting shell is configured and/or trimmed so that (1) an outer surface of the shell does not extend more than 7 mm from the buccal surface of at least the back three teeth of the user's jaw, (2) a rear edge of the shell does not come into contact with tissues to the rear of the rearmost teeth in the user's mouth and (3) upper and lower edges of the mouthpiece do not extend more than 2 mm into the gum line of the user, when the mouthpiece is operatively positioned in the user's mouth; and adding bristles to the shell to produce cleaning of the user's teeth in operation of the mouthpiece appliance.

Figure 1:
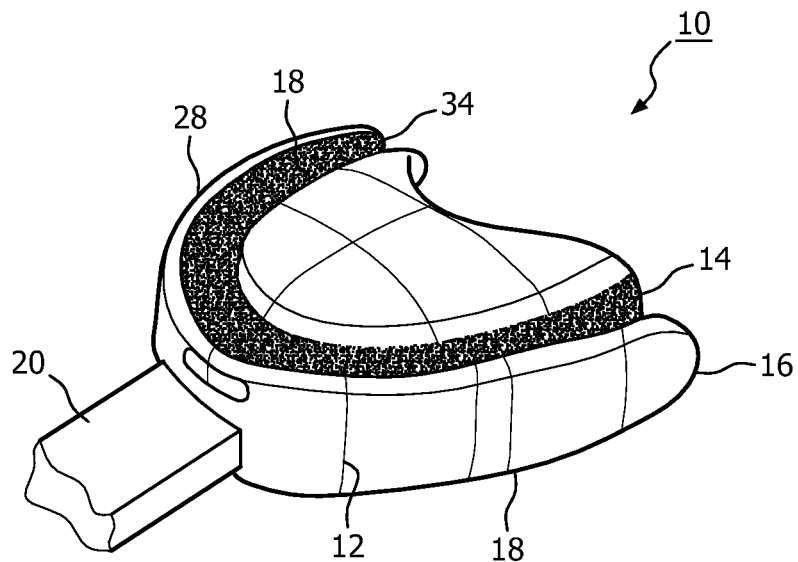
FIG. 1 is a simplified isometric view of a mouthpiece dental oral cleaning appliance.

A conventional mouthpiece for oral cleaning is shown at 10 in FIG. 1. It includes a shell portion 12 which typically is of rigid plastic. The shell portion 12 will typically include upper and lower trays 14, 16 which are configured, respectively, to receive a user's teeth present in their upper and lower jaws. Such a mouthpiece can be adapted to accommodate all of the teeth in both the upper and lower jaws, or just the teeth in one jaw, utilizing one tray, or portions of the teeth in either or both of the jaws. However, for the description below, the mouthpiece will be described as having upper and lower trays which accommodate all of the teeth of the user.

Mounted in the upper and lower trays are bristle portions 18 which in operation contact the teeth for cleaning as the mouthpiece operates. The bristle portions 18 comprise a typical bristle configuration and bristle material (filaments). The mouthpiece 10 is driven by a drive unit which is shown generally at 20. Drive unit 20 typically includes a motor, which operates through linkages to the mouthpiece to move the bristles in a selected motion. Examples of motion include in-and-out, toward and away from the teeth or along the surfaces of the teeth, among others. Drive unit 20 is shown as being positioned outside of the mouthpiece shell portion, but it could be mounted in the mouthpiece itself. The mouthpiece 10 could be sectioned with linkages connected between the drive assembly and each section to provide the desired teeth cleaning action.

As indicated above, however, a generic mouthpiece such as shown in FIG. 1 is designed to accommodate the geometry of a large percentage of users. However, this typically results in relatively few individual users being well accommodated, and a fairly large number of users who are unable to use the mouthpiece effectively. This is due, as noted above, to the wide variety of oral geometries of individual users. Described in detail below is a process and a resulting product by which a mouthpiece may be configured to closely match the geometry of individual users.

Figure 2:
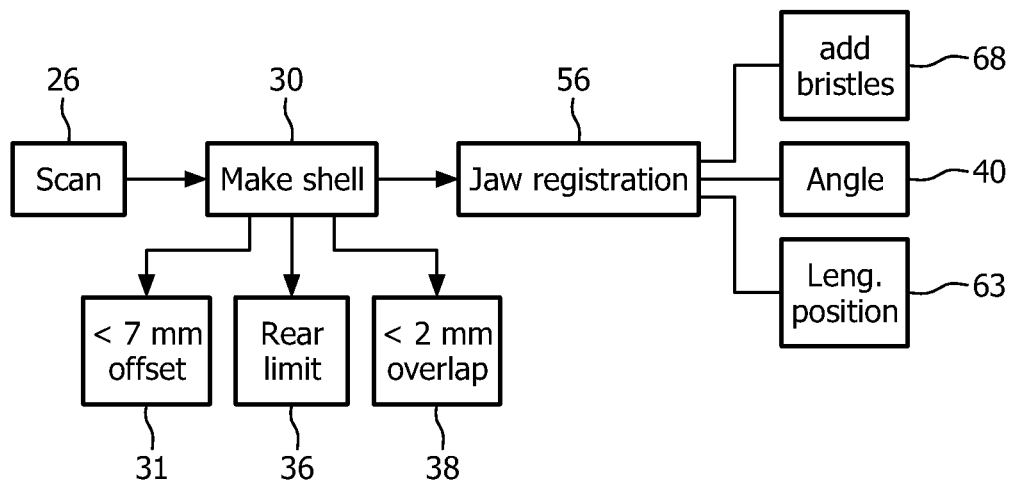
FIG. 2 is a flow chart showing the steps in the process of configuring a mouthpiece to the oral geometry of a particular user.

In a first step, shown at 26 in the flow chart of FIG. 2, the user's complete oral geometry is captured or obtained by the use of an oral digital scanner. Such devices are well know, for instance in orthodontia. One example of such a scanner is made by Cadent. A particular oral scanner is not necessary to the present invention. It need only have the capability of being able to obtain an accurate scan of the user's oral geometry. This step will typically be accomplished by a professional using the oral scanning device. Such a scanning procedure is typically quite fast and produces no discomfort to the user. Alternatively, a scan can be accomplished by taking dental impressions and then having the impressions themselves, or a casting of the impressions, scanned to create the required digital model.

Figure 3:
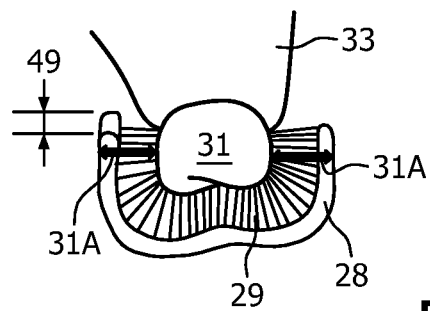
FIG. 3 is an elevational view showing the relationship of the mouthpiece relative to one tooth and the gum line.

Following the scan, a rigid mouthpiece shell is manufactured using known rapid manufacturing techniques, such as SLA prototyping, referred to at Step 30 in FIG. 2. This results in a rigid custom shell for the completed mouthpiece, typically of a plastic material. There are important characteristics of the shell configuration to ensure effective and comfortable operation of the completed mouthpiece. First, the shell should have dimensions, after manufacture in accordance with the scanned oral geometry, and then trimming, such that the outside surface of the shell (28 in FIG. 1) is not offset from the buccal (outside) surface of the teeth by more than 7 mm (i.e. 7 mm or less), particularly for the back three teeth, of both the upper and lower jaws. In some cases, the offset can be more than 7 mm for the remaining teeth, positioned toward the front of the mouth, but even for those teeth, 7 mm or less is still preferred. This dimension has been determined to be important, as it results in a mouthpiece which is convenient for a user to insert into and remove from the mouth, and to be a comfortable overall fit. The step of manufacture of the shell is referred to generally at 30, with the offset characteristic being referred to at 31 in FIG. 2. The 7 mm offset is illustrated in FIG. 3, with the shell indicated at 28, bristles 29, a representative tooth at 31 and the gum at 33. The 7 mm distance is illustrated at 31A.

Figure 4:
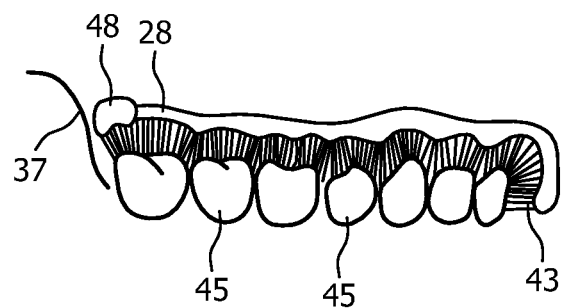
FIG. 4 is a side elevational view showing the mouthpiece relative to the tissue behind the rearmost tooth.
Figure 6:
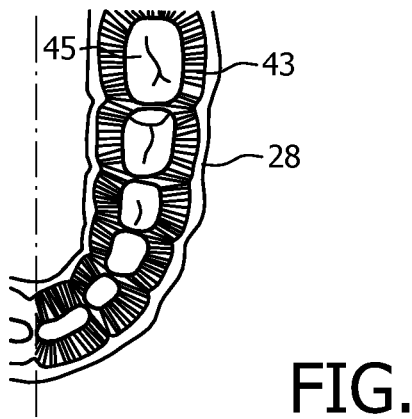
FIG. 6 is a top view showing the relationship of the mouthpiece to a section of teeth.

Further, the shell is configured so that a rearmost edge 34 of the shell does not extend beyond the back edge of the user's rearmost molars to contact the tissue to the rear of the rearmost teeth. Hence, the only material from the mouthpiece which contacts the soft tissues behind the last molars will be bristles or a soft elastomeric member, when the mouthpiece is in place for operation. This is referred to at 36 in FIG. 2, and is shown in FIGS. 4 and 6, with shell 28, rear gum tissue 37, bristles 43, teeth 45 and a soft elastomeric member 48.

Another characteristic of the manufactured shell is a limit of any overlap of the shell relative to the upper and lower gums of 2 mm or less when the mouthpiece is in an operative position in the user's mouth. This is referred to at 38 in FIG. 2 and is shown at 49 in FIG. 3 relative to gum tissue 33. This arrangement is for the comfort of the user, as the gum tissue above 2 mm from the tooth surface is typically quite sensitive. Contact between the hard shell and that area of the gum tissue is undesirable.

In summary, shell 28 is manufactured and then trimmed in accordance with the above configuration guidelines relative to the geometry of each user. The above process results in a mouthpiece having a structure which reflects the specific oral geometry of the individual user.

Figure 5:
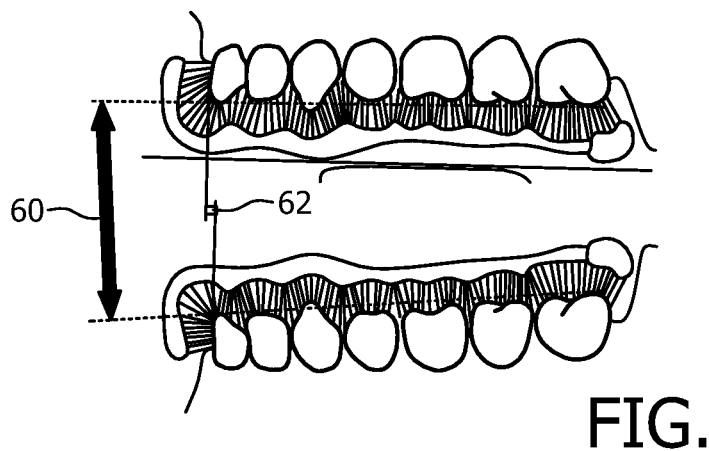
FIG. 5 is an elevational view showing the registration of the upper and lower portions of the mouthpiece.

A further adaptive characteristic of the mouthpiece provided by the scan involves the registration position of the two jaws of the user, referred to as Step 56 in FIG. 2. When a mouthpiece is operatively inserted into a user's mouth, because of different jaw connection geometry, the angle of the two jaws may vary between individual users. There is a particular desired angle for each user. The two trays of the mouthpiece in the shell are arranged (manufactured) at a correct angle provided by the scan so that when the mouthpiece is operatively positioned in the user's mouth, the teeth from the upper and lower jaws are positioned accurately and appropriately within the two trays against the bristles therein. This step is referred to at 40 in FIG. 2 and shown at 60 in FIG. 5. If the jaw angle is not taken into account, the overlap of the shell on the gum line in particular may exceed the 2 mm threshold, which results in a comfort issue for the user, and/or not produce cleaning in the gum line where plaque tends to grow first. The angle of the jaws thus presents both cleaning and comfort issues for a mouthpiece.

Further, with respect to the jaw registration, Step 56, it is important to know the relative longitudinal position of the teeth from the upper and lower jaws when the jaw is closed. If the two jaws are not in longitudinal registry when closed in the mouthpiece, it will produce some resulting discomfort, unless the difference is accommodated in the mouthpiece configuration. Hence, the related longitudinal position of the two tray positions of the mouthpiece is adapted to accommodate the jaw positions of the user, again as determined by the optical scan. This is shown at 62 in FIG. 5 and in Step 63 in FIG. 2. The longitudinal registration of the jaw is more of a comfort issue relative to the user than a cleaning efficacy issue. Lastly, bristles are added in Step 68 in FIG. 2 to the shell to complete the mouthpiece appliance.

Accordingly, the above process and resulting product concerns a mouthpiece which is adapted physically to the oral geometry of a particular user. A process and resulting product have been described which result in a truly effective and comfortable oral care mouthpiece, due to the physical match of the actual appliance and the particular oral geometry of the user's teeth.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A method for optimizing the configuration of a mouthpiece appliance for oral cleaning to the oral geometry of an individual user, comprising the steps of:
    scanning the oral geometry or portions thereof of an individual user; and
    producing a rigid shell member of two portions for the mouthpiece substantially matching the oral geometry scan, an upper tray portion to receive the teeth in the upper jaw and a lower tray portion to receive the teeth in the lower jaw, wherein the resulting shell is configured and/or trimmed so that an outer surface of the shell does not extend more than 7 mm from the buccal surface of at least the back three teeth of the user's jaw, a rear edge of the shell does not come into contact with tissues to the rear of the rearmost teeth in the user's mouth upper and lower edges of the mouthpiece do not extend more than 2 mm into the gum line of the user, when the mouthpiece is operatively positioned in the user's mouth, and the two tray portions of the shell are angled relative to each other to match the angle of the user's jaws when the mouthpiece is operatively positioned in the user's mouth.

2. The method of claim 1, wherein the scan of the oral geometry is a digital scan.

3. The method of claim 1, wherein the outer surface of the shell does not extend more than 7 mm from the buccal or outside surfaces of all of the user's teeth.

4. The method of claim 1, further comprising the step of:
    adding bristles to the shell (68) to produce cleaning of the user's teeth in operation of the mouthpiece appliance.

5. A method for optimizing the configuration of a mouthpiece appliance for oral cleaning to the oral geometry of an individual user, comprising the steps of:
    scanning the oral geometry or portions thereof of an individual user;
    producing a rigid shell member of two tray portions for the mouthpiece substantially matching the oral geometry scan, an upper tray portion to receive the teeth in the upper jaw and a lower tray portion to receive the teeth in the lower jaw, wherein the resulting shell is configured and/or trimmed so that an outer surface of the shell does not extend more than 7 mm from the buccal surface of at least the back three teeth of the user's jaw, a rear edge of the shell does not come into contact with tissues to the rear of the rearmost teeth in the user's mouth and upper and lower edges of the mouthpiece do not extend more than 2 mm into the gum line of the user, when the mouthpiece is operatively positioned in the user's mouth,
    wherein the two tray portions of the shell are arranged so as to match the longitudinal position of the upper and lower jaws of the user in normal position.

6. The method of claim 5, further comprising the step of:
    adding bristles to the shell (68) to produce cleaning of the user's teeth in operation of the mouthpiece appliance.

7. The method of claim 5, wherein the scan of the oral geometry is a digital scan.

8. The method of claim 5, wherein the outer surface of the shell does not extend more than 7 mm from the buccal or outside surfaces of all of the user's teeth.

* * * * *